United States Patent
Muddasani et al.

(10) Patent No.: US 10,626,117 B2
(45) Date of Patent: Apr. 21, 2020

(54) PROCESS FOR THE PREPARATION OF IBRUTINIB

(71) Applicant: NATCO PHARMA LIMITED, Hyderabad (IN)

(72) Inventors: Pulla Reddy Muddasani, Hyderabad (IN); Shankar Reddy Budideti, Hyderabad (IN); Veerababu Madalapu, Hyderabad (IN); Anitha Gattu, Hyderabad (IN); Bala Ankireddy Konda, Hyderabad (IN); Venkaiah Chowdary Nannapaneni, Hyderabad (IN)

(73) Assignee: NATCO PHARMA LIMITED, Hyderabad (IN)

( * ) Notice: Subject to any disclaimer, the term of this patent is extended or adjusted under 35 U.S.C. 154(b) by 0 days.

(21) Appl. No.: 16/074,505

(22) PCT Filed: Feb. 1, 2017

(86) PCT No.: PCT/IN2017/050045
§ 371 (c)(1),
(2) Date: Aug. 1, 2018

(87) PCT Pub. No.: WO2017/134684
PCT Pub. Date: Aug. 10, 2017

(65) Prior Publication Data
US 2019/0241567 A1     Aug. 8, 2019

(30) Foreign Application Priority Data
Feb. 1, 2016  (IN) .............................. 201641003475

(51) Int. Cl.
*A61K 31/519* (2006.01)
*C07D 487/04* (2006.01)
*C07D 473/04* (2006.01)

(52) U.S. Cl.
CPC ......... *C07D 487/04* (2013.01); *C07D 473/04* (2013.01); *C07B 2200/13* (2013.01)

(58) Field of Classification Search
CPC ........................... A61K 31/519; C07D 487/04
USPC ....................... 514/262.1; 544/262
See application file for complete search history.

(56) References Cited

U.S. PATENT DOCUMENTS

| 7,514,444 | B2 | 4/2009 | Honigberg et al. |
| 9,156,847 | B2 | 10/2015 | Pye et al. |
| 9,296,753 | B2 | 5/2016 | Smyth et al. |
| 2013/0115310 | A1 | 5/2013 | Charrier et al. |
| 2014/0323464 | A1 | 10/2014 | Taunton, Jr. et al. |

OTHER PUBLICATIONS

International Search Report and Written Opinion dated May 18, 2017 from International Application No. PCT/IN2017/050045, 7 pages.

*Primary Examiner* — Jeffrey H Murray
(74) *Attorney, Agent, or Firm* — MH2 Technology Law Group, LLP

(57) ABSTRACT

The present invention relates to an improved process for the preparation of Ibrutinib with high purity and high yields. The present process is cost effective and feasible in large scale production also. The present process avoids the mitsunobu reagent conditions also. The present Invention also relates to a process for the preparation of Crystalline form A and Crystalline form C of Ibrutinib.

13 Claims, No Drawings

PROCESS FOR THE PREPARATION OF IBRUTINIB

CROSS-REFERENCE TO RELATED APPLICATIONS

This application is a U.S. National Stage application of PCT/IN2017/050045 filed 1 Feb. 2017, which claims priority to Indian Application No. 201641003475 filed 1 Feb. 2016, the entire disclosures of which are hereby incorporated by reference in their entireties.

FIELD OF THE INVENTION

The present invention relates to an improved process for the preparation of Ibrutinib with high purity and high yields. The present Invention also relates to a process for the preparation of Crystalline form A and form C of Ibrutinib.

BACKGROUND OF THE INVENTION

Ibrutinib is a kinase inhibitor indicated for the treatment of mantle cell lymphoma, chronic lymphocytic leukaemia and waldenstrom's macroglobulinemia.

Ibrutinib is chemically is known as 1-[(3R)-3-[4-amino-3-(4-phenoxyphenyl)-1H-pyrazolo[3,4-d]pyrimidin-1-yl]-1-piperidinyl]-2-propen-1-one and structurally represented as below.

Formula-I

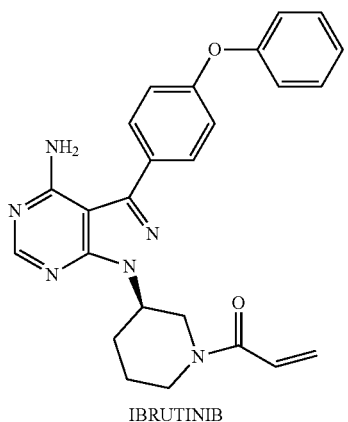

IBRUTINIB

Ibrutinib is first disclosed in U.S. Pat. No. 7,514,444 and marketed as IMBRUVICA®. U.S. Pat. No. '444 is disclosed the Ibrutinib process, wherein 4-amino-3-(4-phenoxyphenyl)-1H-pyrazolo[3,4-d]pyrimidine is reacted with tert-Butyl 3-hydroxypiperidine-1-carboxylate and diisopropyl diazodicarboxylate to obtain intermediate under mitsunobu reaction conditions by converting the hydroxy moiety of the tert-Butyl 3-hydroxypiperidine-1-carboxylate to a better leaving group, thereby allowing a substitution reaction. Further it is converted to ibrutinib by deprotection of Boc and acylation with acryl chloride. The reaction steps as illustrated by the following scheme I:

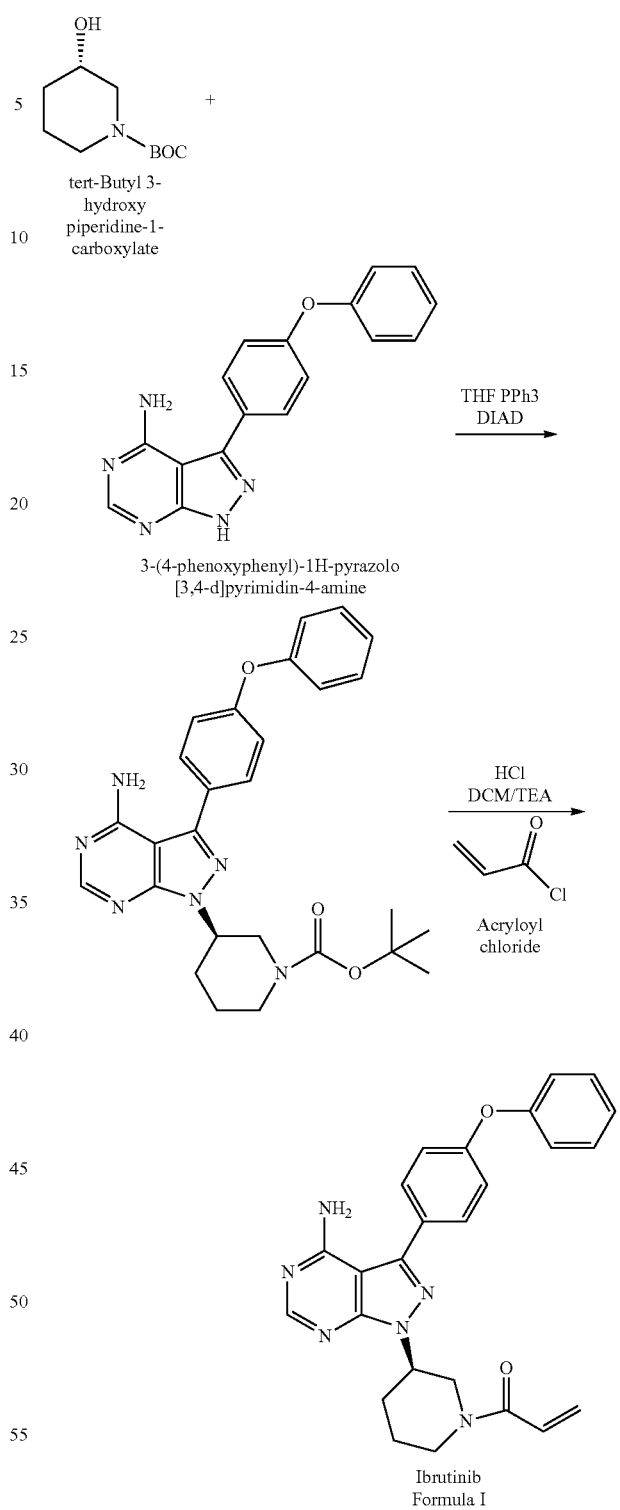

U.S. Pat. No. 9,156,847 has disclosed another process for the preparation of ibrutinib intermediate, wherein the pyrazolo [3,4-D] pyridine-4-amine ring of ibrutinib is preared through cyclization with use of formamide acetate and the reaction steps are illustrated in the below scheme II:

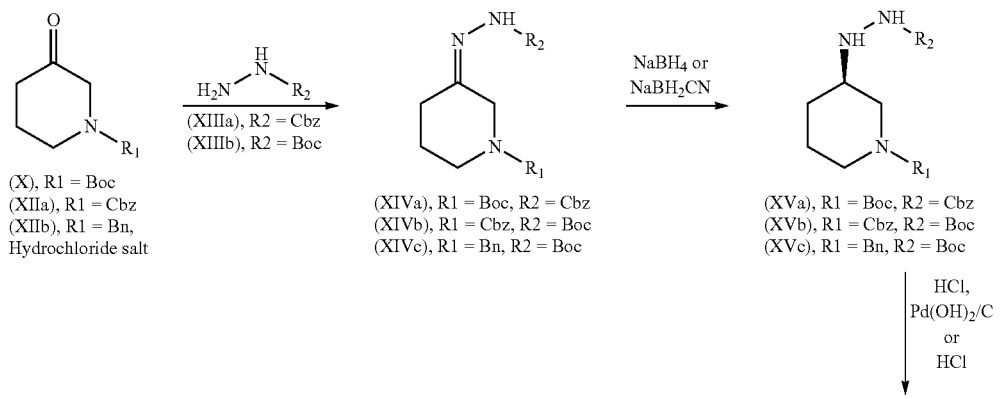
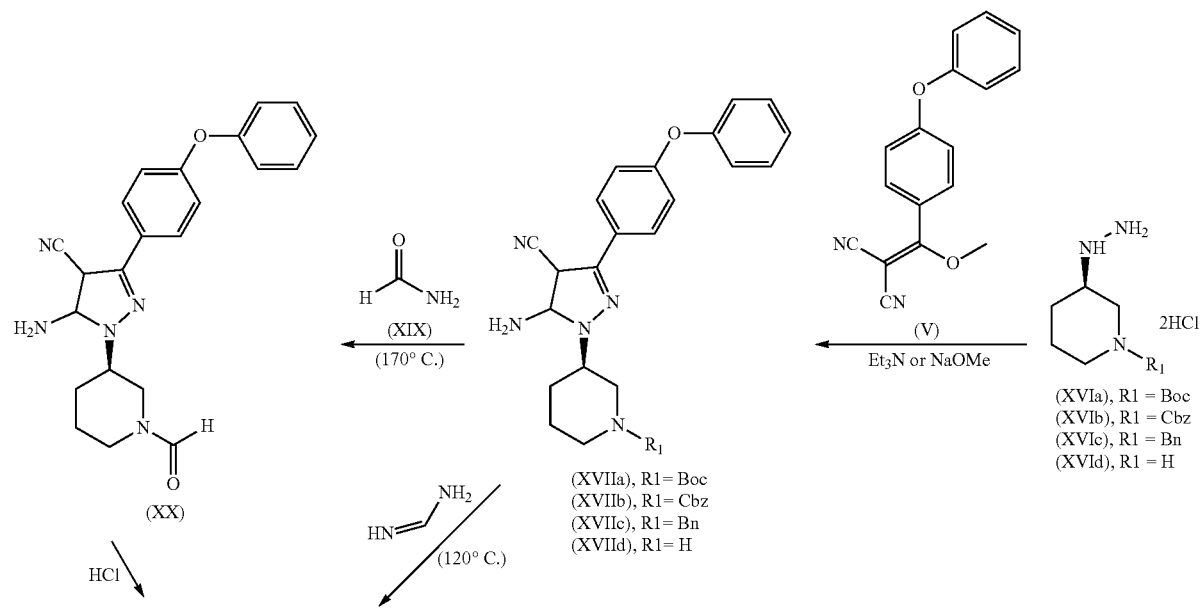
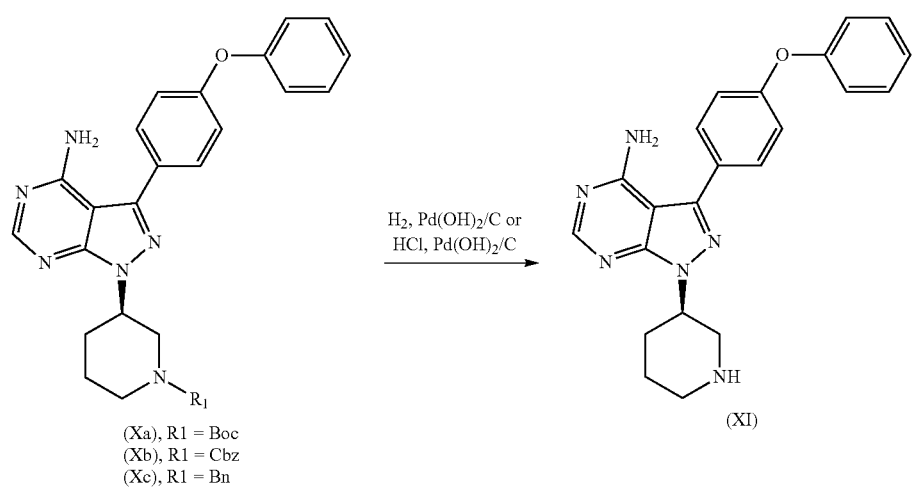

According to this patent the process which is disclosed in U.S. Pat. No. 7,514,444 has a number of disadvantages, such as those associated with cost, efficiency and environmental disadvantages. For instance the Mitsunobu step may be wasteful, costly and cumbersome.

U.S. Pat. No. 9,296,753 has disclosed the crystalline forms A, B, C, D, E and F and their process for the preparation.

The present inventors of the present invention has developed an improved process for the preparation of Ibrutinib with high yield and high purity. The present process is cost effective and feasible in large scale production also. The present process avoids the mitsunobu reagent conditions also.

SUMMARY OF THE PRESENT INVENTION

One aspect of the present invention is to provide a process for the preparation of ibrutinib comprising the steps of:
  a) reacting (S)-1-boc-3-hydroxy piperidine with methane sulfonyl chloride to get (S)-1-boc-3-methylsulfonyloxy piperidine,
  b) treating (S)-1-boc-3-methylsulfonyloxy piperidine with 3-(4-phenoxyphenyl)-1H-pyrazolo[3,4-d]pyrimidine-4-amine in presence of inorganic base or mixture of inorganic bases to get (R)-3-(4-phenoxyphenyl)-1-(piperidin-3-yl-1H-pyrazolo[3,4-d]pyrimidine-4-amine hydrochloride,
  c) reacting (R)-3-(4-phenoxyphenyl)-1-(piperidin-3-yl-1H-pyrazolo[3,4-d]pyrimidine-4-amine hydrochloride with base followed by acryloyl chloride to obtain ibrutinib,
  d) optionally purifying the ibrutinib.

Another aspect of the present Invention is to provide a process for the preparation of Ibrutinib Crystalline form A comprising the steps of:
  a) reacting (S)-1-boc-3-hydroxy piperidine with methane sulfonyl chloride to get (S)-1-boc-3-methylsulfonyloxy piperidine,
  b) treating (S)-1-boc-3-methylsulfonyloxy piperidine with 3-(4-phenoxyphenyl)-1H-pyrazolo[3,4-d]pyrimidine-4-amine in presence of inorganic base or mixture of inorganic bases to get (R)-3-(4-phenoxyphenyl)-1-(piperidin-3-yl-1H-pyrazolo[3,4-d]pyrimidine-4-amine hydrochloride,
  c) reacting (R)-3-(4-phenoxyphenyl)-1-(piperidin-3-yl-1H-pyrazolo[3,4-d]pyrimidine-4-amine hydrochloride with base followed by acryloyl chloride to obtain ibrutinib,
  d) optionally purifying the ibrutinib.
  e) dissolving ibrutinib in polar aprotic solvent and
  f) isolating Crystalline form A of ibrutinib.

Yet another aspect of the present Invention is to provide a process for the preparation of Ibrutinib Crystalline form C comprising the steps of:
  a) reacting (S)-1-boc-3-hydroxy piperidine with methane sulfonyl chloride to get (S)-1-boc-3-methylsulfonyloxy piperidine,
  b) treating (S)-1-boc-3-methylsulfonyloxy piperidine with 3-(4-phenoxyphenyl)-1H-pyrazolo[3,4-d]pyrimidine-4-amine in presence of inorganic base or mixture of inorganic bases to get (R)-3-(4-phenoxyphenyl)-1-(piperidin-3-yl-1H-pyrazolo[3,4-d]pyrimidine-4-amine hydrochloride,
  c) reacting (R)-3-(4-phenoxyphenyl)-1-(piperidin-3-yl-1H-pyrazolo[3,4-d]pyrimidine-4-amine hydrochloride with base followed by acryloyl chloride to obtain ibrutinib,
  d) optionally purifying the ibrutinib.
  e) dissolving ibrutinib in polar protic solvent and
  f) isolating Crystalline form A of ibrutinib.

Yet another aspect of the present invention is to provide a purification of ibrutinib comprising the steps of:
  a) dissolving ibrutinib in non-polar solvent or polar aprotic solvent or mixture thereof and
  b) isolating pure ibrutinib.

Yet another aspect of the present invention is to provide a process for the preparation of Crystalline form A of Ibrutinib comprising the steps of:
  a) dissolving ibrutinib in polar aprotic solvent and
  b) isolating Crystalline form A of ibrutinib.

Yet another aspect of the present invention is to provide a process for the preparation of Crystalline form C of Ibrutinib comprising the steps of:
  a) dissolving ibrutinib in polar protic solvent and
  b) isolating Crystalline form C of ibrutinib.

Yet another aspect of the present invention is to provide a process for the purification of ibrutinib comprising the steps of:
  a) dissolving ibrutinib in methylene chloride and toluene, and
  b) isolating pure ibrutinib.

DETAILED DESCRIPTION OF THE INVENTION

The present invention is related to an improved process for the preparation of Ibrutinib, wherein reacting (S)-1-boc-3-hydroxy piperidine with methane sulfonyl chloride to get (S)-1-boc-3-methylsulfonyloxy piperidine and treating (S)-1-boc-3-methylsulfonyloxy piperidine with 3-(4-phenoxyphenyl)-1H-pyrazolo[3,4-d]pyrimidine-4-amine in presence of inorganic base or mixture of inorganic bases to get (R)-3-(4-phenoxyphenyl)-1-(piperidin-3-yl-1H-pyrazolo[3,4-d]pyrimidine-4-amine hydrochloride and converted to ibrutinib reacting with acryloyl chloride. Further ibrutinib is converted to crystalline form A and crystalline form C.

One embodiment of the present invention is to provide a process for the preparation of ibrutinib comprising the steps of:
  a) reacting (S)-1-boc-3-hydroxy piperidine with methane sulfonyl chloride to get (S)-1-boc-3-methylsulfonyloxy piperidine,
  b) treating (S)-1-boc-3-methylsulfonyloxy piperidine with 3-(4-phenoxyphenyl)-1H-pyrazolo[3,4-d]pyrimidine-4-amine in presence of inorganic base or mixture of inorganic bases to get (R)-3-(4-phenoxyphenyl)-1-(piperidin-3-yl-1H-pyrazolo[3,4-d]pyrimidine-4-amine hydrochloride,
  c) reacting (R)-3-(4-phenoxyphenyl)-1-(piperidin-3-yl-1H-pyrazolo[3,4-d]pyrimidine-4-amine hydrochloride with base followed by acryloyl chloride to obtain ibrutinib,
  d) optionally purifying the ibrutinib.

The present invention is shown in the below scheme:

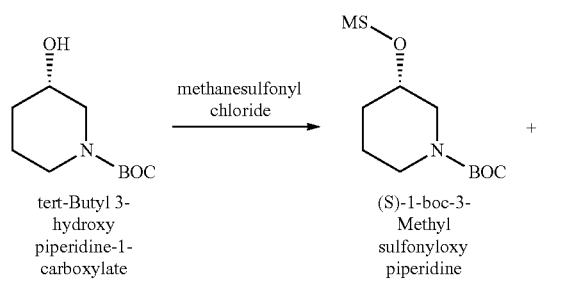

tert-Butyl 3-hydroxy piperidine-1-carboxylate (S)-1-boc-3-Methyl sulfonyloxy piperidine

+

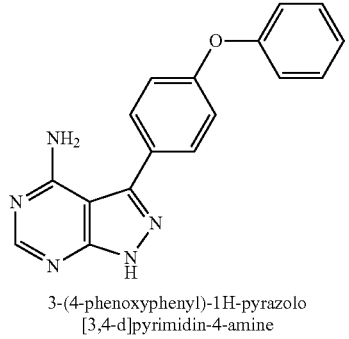

3-(4-phenoxyphenyl)-1H-pyrazolo [3,4-d]pyrimidin-4-amine

Inorganic base or mixture of inorganic bases

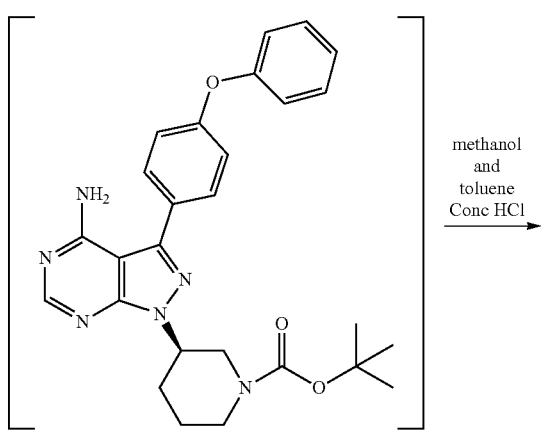

methanol and toluene Conc HCl

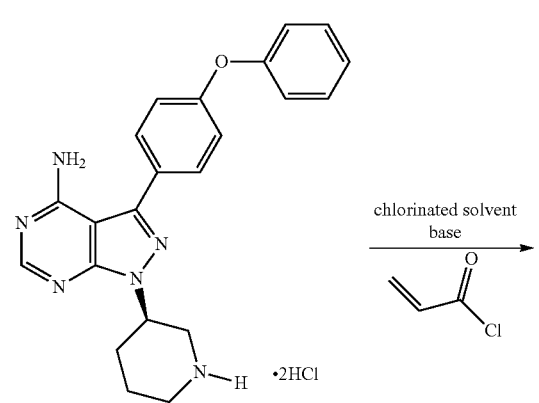

3-(4-phenoxyphenyl)-1-[(3R)-3-piperidyl]pyrazolo [3,4-d]pyrimidin-4-amine Hydro chloride ·2HCl chlorinated solvent base

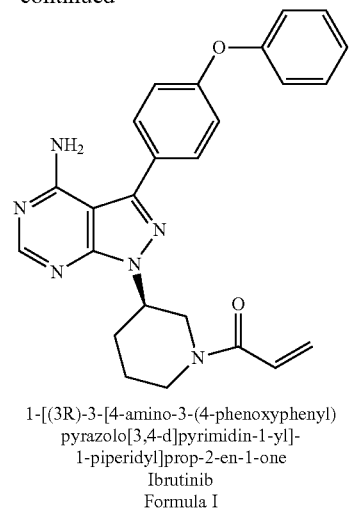

1-[(3R)-3-[4-amino-3-(4-phenoxyphenyl) pyrazolo[3,4-d]pyrimidin-1-yl]-1-piperidyl]prop-2-en-1-one
Ibrutinib
Formula I According to the present invention, triethylamine is added to the reaction mixture of (S)-1-Boc-3-hydroxypiperidin and methanesulfonyl chloride in methylenechloride at −10 to 10° C. The reaction mass is allowed to ambient temperature and stirred for 30 min and washed with water The organic layer is concentrated, stirred with hexane, filtered the solid and dried to yield (S)-1-boc-3-methylsulfonyloxy piperidine.

The solution of (S)-1-boc-3-methylsulfonyloxy piperidine in dimethylacetamide is added to the reaction mixture of 3-(4-phenoxyphenyl)-1H-pyrazolo [3, 4-d] pyrimidine-4-amine, inorganic base and another inorganic base in N-methyl pyrrolidine at 45-60° C. The reaction mass is heated to 75-90° C., stirred for 14 h, filtered and concentrated. The concentrated mass is dissolved in 1:1 mixture of methanol-toluene and added hydrochloric acid. The reaction mixture is stirred for 4-6 h at 35-50° C., separated the aqueous layer and concentrated under vacuum. The concentrated mass is stirred with methanol and ethyl acetate, filtered the solid and dried. The resulting dried product is dissolved in DM water and added to sodium carbonate solution and Ethyl acetate mixture. The product is filtered, washed with DM water and then the wet product is dissolved in Con.HCl and methanol mixture. The resulting reaction mass is concentrated, stirred with methanol and ethyl acetate The product is filtered, washed and dried to to yield (R)-3-(4-phenoxyphenyl)-1-(piperidin-3-yl-1H-pyrazolo [3, 4-d] pyrimidine-4-amine hydrochloride.

The solution of (S)-1-boc-3-methylsulfonyloxy piperidine in dimethylacetamide is added to the reaction mixture of 3-(4-phenoxyphenyl)-1H-pyrazolo [3, 4-d]pyrimidine-4-amine, inorganic base and another inorganic base in dimethylacetamide at 45-60° C. The reaction mass is heated to 75-90° C., stirred for 14 h, filtered and concentrated. The concentrated mass is dissolved in 1:1 mixture of methanol-toluene and added hydrochloric acid. The reaction mixture is stirred for 4-6 h at 35-50° C., separated the aqueous layer and concentrated under vacuum. The concentrated mass is stirred with methanol and ethyl acetate, filtered the solid and dried to yield (R)-3-(4-phenoxyphenyl)-1-(piperidin-3-yl-1H-pyrazolo [3, 4-d] pyrimidine-4-amine hydrochloride.

The solution of (S)-1-boc-3-methylsulfonyloxy piperidine in dimethylacetamide is added to the reaction mixture of 3-(4-phenoxyphenyl)-1H-pyrazolo [3, 4-d] pyrimidine-4-amine, inorganic base in dimethylacetamide at 45-55° C.

The reaction mass is heated to 80-90° C., stirred for 14 h, filtered and concentrated. The concentrated mass is dissolved in 1:1 mixture of methanol-toluene and added hydrochloric acid. The reaction mixture is stirred for 5-6 h at 40-50° C., separated the aqueous layer and concentrated under vacuum. The concentrated mass is stirred with methanol and ethyl acetate, filtered the solid and dried to yield (R)-3-(4-phenoxyphenyl)-1-(piperidin-3-yl-1H-pyrazolo [3,4-d] pyrimidine-4-amine hydrochloride.

Acryloyl chloride is dissolved in methylene chloride and added to the cold reaction mixture of (R)-3-(4-phenoxyphenyl)-1-(piperidin-3-yl-1H-pyrazolo [3, 4-d] pyrimidine-4-amine hydrochloride and base in methylene chloride at −75 to −85° C. The reaction mass is stirred for 10 min at −80 to −90° C. and washed with aqueous citric acid solution followed by aqueous sodium bicarbonate solution and water. The organic layer is concentrated, stirred with ethyl acetate and hexane, filtered the solid and dried to yield Ibrutinib.

Acryloyl chloride is dissolved in methylene chloride and added to the cold reaction mixture of (R)-3-(4-phenoxyphenyl)-1-(piperidin-3-yl-1H-pyrazolo [3, 4-d] pyrimidine-4-amine hydrochloride and base in methylene chloride at −75 to −85° C. The reaction mass is stirred for 10 min at −80 to −90° C. and washed with aqueous citric acid solution followed by aqueous sodium bicarbonate solution and water. The organic layer is concentrated, to yield syrupy mass and dissolved in MDC and then added Toluene to crystallize product. The solid product is filtered and dried to yield Ibrutinib.

According to the present invention, Inorganic bases is selected from cesium carbonate, potassium carbonate, sodium carbonate, sodium bicarbonate, sodium phosphate, potassium phosphate, potassium phosphate, sodium acetate, potassium acetate, preferably potassium carbonate and cesium carbonate.

According to the present invention, base employed in step c) is selected from diisopropylethylamine and trimethylamine, preferably diisopropylethylamine.

Another embodiment of the present invention is to provide a purification of ibrutinib comprising the steps of:
 a) dissolving ibrutinib in non-polar solvent or polar aprotic solvent or mixture thereof and
 b) isolating pure ibrutinib.

According to the present invention, non-polar solvent is selected from pentane, hexane, toluene and cyclophexane, preferably hexane.

According to the present invention, polar aprotic solvent is selected from tetrahydrofuran, ethyl acetate and dimethyl formamide, preferably ethylacetate.

Yet another embodiment of the present Invention is to provide a process for the preparation of Ibrutinib Crystalline form A comprising the steps of:
 a) reacting (S)-1-boc-3-hydroxy piperidine with methane sulfonyl chloride to get (S)-1-boc-3-methylsulfonyloxy piperidine,
 b) treating (S)-1-boc-3-methylsulfonyloxy piperidine with 3-(4-phenoxyphenyl)-1H-pyrazolo[3,4-d]pyrimidine-4-amine in presence of inorganic base or mixture of inorganic bases to get (R)-3-(4-phenoxyphenyl)-1-(piperidin-3-yl-1H-pyrazolo[3,4-d]pyrimidine-4-amine hydrochloride,
 c) reacting (R)-3-(4-phenoxyphenyl)-1-(piperidin-3-yl-1H-pyrazolo[3,4-d]pyrimidine-4-amine hydrochloride with base followed by acryloyl chloride to obtain ibrutinib,
 d) optionally purifying the ibrutinib.
 e) dissolving ibrutinib in polar aprotic solvent and
 f) isolating Crystalline form A of ibrutinib.

Yet another embodiment of the present invention is to provide a process for the preparation of Crystalline form A of Ibrutinib comprising the steps of:
 a) dissolving ibrutinib in polar aprotic solvent and
 b) isolating Crystalline form A of ibrutinib.

According to the present invention, polar aprotic solvent is selected from methylene chloride, ethyl acetate, acetone preferably ethyl acetate.

Yet another embodiment of the present Invention is to provide a process for the preparation of Ibrutinib Crystalline form C comprising the steps of:
 a) reacting (S)-1-boc-3-hydroxy piperidine with methane sulfonyl chloride to get (S)-1-boc-3-methylsulfonyloxy piperidine,
 b) treating (S)-1-boc-3-methylsulfonyloxy piperidine with 3-(4-phenoxyphenyl)-1H-pyrazolo[3,4-d]pyrimidine-4-amine in presence of inorganic base or mixture of inorganic bases to get (R)-3-(4-phenoxyphenyl)-1-(piperidin-3-yl-1H-pyrazolo[3,4-d]pyrimidine-4-amine hydrochloride,
 c) reacting (R)-3-(4-phenoxyphenyl)-1-(piperidin-3-yl-1H-pyrazolo[3,4-d]pyrimidine-4-amine hydrochloride with base followed by acryloyl chloride to obtain ibrutinib,
 d) optionally purifying the ibrutinib.
 e) dissolving ibrutinib in polar protic solvent and
 f) isolating Crystalline form C of ibrutinib.

Yet another embodiment of the present invention is to provide a process for the preparation of Crystalline form C of Ibrutinib comprising the steps of:
 a) dissolving ibrutinib in polar protic solvent and
 b) isolating Crystalline form C of ibrutinib.

According to the present invention, polar protic solvent is selected from methanol, ethanol, n-propanol preferably methanol.

Yet another embodiment of the present invention is to provide a process for the purification of ibrutinib comprising the steps of:
 a) dissolving ibrutinib in methylene chloride and toluene, and
 b) isolating pure ibrutinib.

The following examples are provided for illustrative purpose only and are not intended to limit the scope of invention in anyway.

EXAMPLE-1

Preparation of (S)-1-Boc-3-Methylsulfonyloxy Piperidine

Triethylamine (120.7 g) was added to the reaction mixture of (S)-1-Boc-3-hydroxypiperidin (200 g) and methanesulfonyl chloride (125.3 g) in methylenechloride (2000 ml) at 0° C. The reaction mass was allowed to ambient temperature and stirred for 30 min and washed with water (2×2 l). The organic layer was concentrated, stirred with hexane (1.4 l), filtered the solid and dried to yield (S)-1-boc-3-methylsulfonyloxy piperidine (265 g; 96.0%).

EXAMPLE-2

Preparation of (S)-1-boc-3-Methylsulfonyloxy Piperidine

Triethylamine (120.7 g) was added to the reaction mixture of (S)-1-Boc-3-hydroxypiperidin (200 g) and methanesulfonyl chloride (125.3 g) in methylenechloride (2000 ml) at 0° C. The reaction mass was allowed to ambient temperature and stirred for 30 min and washed with water (2×2 l). The organic layer was concentrated, stirred with mixture of methylene chloride (120.0 ml) and hexane (1.4 l), filtered the solid and dried to yield (S)-1-boc-3-methylsulfonyloxy piperidine (254.0 g; 91.2%).

HPLC Purity: 99.5%; chiral purity: 100%

EXAMPLE-3

Preparation of (R)-3-(4-Phenoxyphenyl)-1-(Piperidin-3-Yl-1H-Pyrazolo[3,4-d]Pyrimidine-4-Amine Hydrochloride The solution of (S)-1-boc-3-methylsulfonyloxy piperidine (173.3 g) in N-methyl-2-pyrrolidone (525 ml) was added to the reaction mixture of 3-(4-phenoxyphenyl)-1H-pyrazolo[3,4-d]pyrimidine-4-amine (75 g), cesium carbonate (217.7 g) in N-methyl-2-pyrrolidone (600 ml) at 55° C. The reaction mass was heated to 80-85° C., stirred for 6-8 h, water workup and partially concentrated. The partial concentrated mass was dissolved in methanol (935 ml) and added hydrochloric acid (186 ml; 18% w/v). The reaction mixture was stirred for 4-6 h at 45° C., separated the aqueous layer and concentrated under vacuum. The concentrated mass was stirred with methanol (225 ml) and ethyl acetate (975 ml), filtered the solid and dried. The resulting dried product was dissolved in DM water (800 ml) and added to sodium carbonate (55.4 g) solution and Ethyl acetate (160 ml) mixture. The product was filtered, washed with DM water and then the wet product was dissolved in Con.HCl (69 ml) and methanol (375 ml) mixture. The resulting reaction mass was concentrated, stirred with methanol (255 ml) and ethyl acetate (425 ml). The product was filtered, washed and dried to yield (R)-3-(4-phenoxyphenyl)-1-(piperidin-3-yl-1H-pyrazolo[3,4-d]pyrimidine-4-amine hydrochloride (69 g; 60.7%).

HPLC Purity: 99.9%; chiral purity: 99.9%

EXAMPLE-4

Preparation of (R)-3-(4-Phenoxyphenyl)-1-(Piperidin-3-Yl-1H-Pyrazolo[3,4-d]Pyrimidine-4-Amine Hydrochloride The solution of (S)-1-boc-3-methylsulfonyloxy piperidine (115.5 g) in dimethylacetamide (300 ml) was added to the reaction mixture of 3-(4-phenoxyphenyl)-1H-pyrazolo [3,4-d]pyrimidine-4-amine (50 g), cesium carbonate (13.4 g) and potassium carbonate (108.3 g) in dimethylacetamide (450 ml) at 55° C. The reaction mass was heated to 85° C., stirred for 14 h, filtered and concentrated. The concentrated mass was dissolved in 1:1 mixture of methanol-toluene (1250 ml) and added hydrochloric acid (117 ml; 18% w/v). The reaction mixture was stirred for 6 h at 45° C., separated the aqueous layer and concentrated under vacuum. The concentrated mass was stirred with methanol (100 ml) and ethyl acetate (625 ml), filtered the solid and dried to yield (R)-3-(4-phenoxyphenyl)-1-(piperidin-3-yl-1H-pyrazolo[3,4-d]pyrimidine-4-amine hydrochloride (59 g; 78.4%).

HPLC Purity: 99.6%

EXAMPLE-5

Preparation of (R)-3-(4-Phenoxyphenyl)-1-(Piperidin-3-Yl-1H-Pyrazolo[3,4-d]Pyrimidine-4-Amine Hydrochloride The solution of (S)-1-boc-3-methylsulfonyloxy piperidine (11.55 g) in dimethylacetamide (20 ml) was added to the reaction mixture of 3-(4-phenoxyphenyl)-1H-pyrazolo [3,4-d]pyrimidine-4-amine (5 g) and potassium carbonate (6.15 g) in dimethylacetamide (55 ml) at 55° C. The reaction mass was heated to 100° C., stirred for 28 h, filtered and concentrated. The concentrated mass was dissolved in 1:1 mixture of methanol-toluene (86 ml) and added hydrochloric acid (86 ml; 18% w/v). The reaction mixture was stirred for 30 h at 25° C., separated the aqueous layer and concentrated under vacuum. The concentrated mass was stirred with ethyl acetate (65 ml), filtered the solid and dried to yield (R)-3-(4-phenoxyphenyl)-1-(piperidin-3-yl-1H-pyrazolo[3,4-d] pyrimidine-4-amine hydrochloride (3.5 g; 46.1%).

HPLC Purity: 98.5%

EXAMPLE-6

Preparation of (R)-3-(4-Phenoxyphenyl)-1-(Piperidin-3-Yl-1H-Pyrazolo [3, 4-d] Pyrimidine-4-Amine (Ibrutinib)

Acryloyl chloride (9.85 g) was dissolved in methylene chloride (150 ml) and added to the cold reaction mixture of (R)-3-(4-phenoxyphenyl)-1-(piperidin-3-yl-1H-pyrazolo [3, 4-d] pyrimidine-4-amine hydrochloride (50 g) and diisopropylethylamine (63.2 g) in methylene chloride (1000 ml) at −85° C. The reaction mass was stirred for 10 min at −85° C. and washed with aqueous citric acid solution (500 ml; 5% w/w) followed by aqueous sodium bicarbonate solution (500 ml; 5% w/w) and water (500 ml). The organic layer was concentrated, stirred with ethyl acetate (300 ml) and hexane (300 ml), filtered the solid and dried to yield (R)-3-(4-phenoxyphenyl)-1-(piperidin-3-yl-1H-pyrazolo[3,4-d]pyrimidine-4-amine crude (40.6 g; 84.8%).

HPLC Purity: 99.7%

EXAMPLE-7

Preparation of (R)-3-(4-Phenoxyphenyl)-1-(Piperidin-3-Yl-1H-Pyrazolo [3, 4-d] Pyrimidine-4-Amine (Ibrutinib)

Acryloyl chloride (1 g) was dissolved in methylene chloride (10 ml) and added to the cold reaction mixture of (R)-3-(4-phenoxyphenyl)-1-(piperidin-3-yl-1H-pyrazolo [3, 4-d] pyrimidine-4-amine hydrochloride (5 g) and diisopropylethylamine (5.6 g) in methylene chloride (75 ml) at −45° C. The reaction mass was stirred for 30 min at −45° C. and washed with aqueous citric acid solution (50 ml; 5% w/w) followed by aqueous sodium bicarbonate solution (50 ml; 5% w/w) and water (50 ml). The organic layer was concentrated, stirred with ethyl acetate (30 ml), filtered the solid and dried to yield (R)-3-(4-phenoxyphenyl)-1-(piperidin-3-yl-1H-pyrazolo[3,4-d]pyrimidine-4-amine crude (2.9 g; 60.6%).

EXAMPLE-8

Preparation of 1-[(3R)-3-[4-Amino-3-(4-Phenoxyphenyl)-Pyrazolo-[3,4-d]Pyrimidin-1-Yl]-1-Piperidyl]Prop-2-En-1-One) (Ibrutinib)

Acryloyl chloride (10.34 g) was dissolved in methylene chloride (50 ml) and added to the cold reaction mixture of (R)-3-(4-phenoxyphenyl)-1-(piperidin-3-yl-1H-pyrazolo[3, 4-d]pyrimidine-4-amine hydrochloride (50 g) and diisopropylethylamine (63.3 g) in methylene chloride (1000 ml) at −85° C. The reaction mass was stirred for 10 min at −85° C.

and washed with aqueous citric acid solution (2×500 ml; 5% w/w) followed by aqueous sodium bicarbonate solution (500 ml; 2% w/w) and water (500 ml). The organic layer was concentrated to yield syrupy mass and dissolved in MDC (50 ml) and then added Toluene (400 ml) to crystallize product. The solid product was filtered and dried to yield 1-[(3R)-3-[4-Amino-3-(4-Phenoxyphenyl)-Pyrazolo-[3,4-d]Pyrimidin-1-Yl]-1-Piperidyl]Prop-2-en-1-one (51 g) HPLC Purity: 99.8%; chiral purity: 99.9%.

EXAMPLE-9

Preparation Ibrutinib Form—A

1-[(3R)-3-[4-Amino-3-(4-Phenoxyphenyl)-Pyrazolo-[3,4-d]Pyrimidin-1-Yl]-1-Piperidyl]Prop-2-en-1-one (5.0 g), was dissolved in ethyl acetate (35 ml) at 25-35° C., filtered and crystallized from ethyl acetate. The product was filtered, washed and dried to yield pure Ibrutinib crystalline Form-A (3.3 g)

EXAMPLE-10

Preparation Ibrutinib Pharma Form—C

1-[(3R)-3-[4-Amino-3-(4-Phenoxyphenyl)-Pyrazolo-[3,4-d]Pyrimidin-1-Yl]-1-Piperidyl]Prop-2-en-1-one (70.0 g) was dissolved in methanol (875 ml) at 50-55° C., filtered and crystallized from methanol. The product was filtered, washed and dried to yield pure Ibrutinib crystalline Form-C (51 g; 72.8%).

HPLC Purity: 99.68%; chiral purity: 99.9%.

We claim:

1. A process for the preparation of Ibrutinib comprising the steps of:
    a) reacting (S)-1-boc-3-hydroxy piperidine with methane sulfonyl chloride to get (S)-1-boc-3-methylsulfonyloxy piperidine,
    b) treating (S)-1-boc-3-methylsulfonyloxy piperidine with 3-(4-phenoxyphenyl)-1H-pyrazolo[3,4-d]pyrimidine-4-amine in presence of inorganic base or mixture of inorganic bases to get (R)-3-(4-phenoxyphenyl)-1-(piperidin-3-yl-1H-pyrazolo[3,4-d]pyrimidine-4-amine hydrochloride,
    c) reacting (R)-3-(4-phenoxyphenyl)-1-(piperidin-3-yl-1H-pyrazolo[3,4-d]pyrimidine-4-amine hydrochloride with base followed by acryloyl chloride to obtain ibrutinib,
    d) optionally purifying the ibrutinib.

2. A process according to claim 1, wherein the inorganic base is selected from cesium carbonate, potassium carbonate, sodium carbonate, sodium bicarbonate, sodium phosphate, potassium phosphate, potassium phosphate, sodium acetate, potassium acetate.

3. A process according to claim 1, wherein the base employed in step c) is selected from diisopropylethylamine and trimethylamine.

4. The process for the preparation of Ibrutinib Crystalline form A comprising the steps of:
    a) reacting (S)-1-boc-3-hydroxy piperidine with methane sulfonyl chloride to get (S)-1-boc-3-methylsulfonyloxy piperidine,
    b) treating (S)-1-boc-3-methylsulfonyloxy piperidine with 3-(4-phenoxyphenyl)-1H-pyrazolo[3,4-d]pyrimidine-4-amine in presence of inorganic base or mixture of inorganic bases to get (R)-3-(4-phenoxyphenyl)-1-(piperidin-3-yl-1H-pyrazolo[3,4-d]pyrimidine-4-amine hydrochloride,
    c) reacting (R)-3-(4-phenoxyphenyl)-1-(piperidin-3-yl-1H-pyrazolo[3,4-d]pyrimidine-4-amine hydrochloride with base followed by acryloyl chloride to obtain ibrutinib,
    d) optionally purifying the ibrutinib,
    e) dissolving ibrutinib in polar aprotic solvent and
    f) isolating Crystalline form A of ibrutinib.

5. A process according to claim 4, wherein the inorganic base is selected from cesium carbonate, potassium carbonate, sodium carbonate, sodium bicarbonate, sodium phosphate, potassium phosphate, potassium phosphate, sodium acetate, potassium acetate.

6. A process according to claim 4, wherein, base employed in step c) is selected from diisopropylethylamine and trimethylamine.

7. A process according to claim 4, wherein the polar aprotic solvent is selected from methylene chloride, ethyl acetate.

8. A process according to claim 4 wherein the ibrutinib is purified, and wherein step d) comprises the steps of:
    i) dissolving ibrutinib in methylene chloride and toluene, and
    ii) isolating pure ibrutinib.

9. A process for the preparation of Crystalline form C of Ibrutinib comprising the steps of:
    a) dissolving ibrutinib in polar protic solvent and
    b) isolating Crystalline form C of ibrutinib.

10. The process for the preparation of Ibrutinib Crystalline form C according to claim 9 comprising the steps of:
    a) reacting (S)-1-boc-3-hydroxy piperidine with methane sulfonyl chloride to get (S)-1-boc-3-methylsulfonyloxy piperidine,
    b) treating (S)-1-boc-3-methylsulfonyloxy piperidine with 3-(4-phenoxyphenyl)-1H-pyrazolo[3,4-d]pyrimidine-4-amine in presence of inorganic base or mixture of inorganic bases to get (R)-3-(4-phenoxyphenyl)-1-(piperidin-3-yl-1H-pyrazolo[3,4-d]pyrimidine-4-amine hydrochloride,
    c) reacting (R)-3-(4-phenoxyphenyl)-1-(piperidin-3-yl-1H-pyrazolo[3,4-d]pyrimidine-4-amine hydrochloride with base followed by acryloyl chloride to obtain ibrutinib,
    d) optionally purifying the ibrutinib,
    e) dissolving ibrutinib in polar protic solvent and
    f) isolating Crystalline form C of ibrutinib.

11. A process according to claim 10, wherein the inorganic base is selected from cesium carbonate, potassium carbonate, sodium carbonate, sodium bicarbonate, sodium phosphate, potassium phosphate, potassium phosphate, sodium acetate, potassium acetate.

12. A process according to claim 10, wherein, base employed in step c) is selected from diisopropylethylamine and trimethylamine.

13. A process according claim 9, wherein the polar protic solvent is selected from methanol, ethanol, n-propanol.

* * * * *